United States Patent [19]

Van Wijck et al.

[11] Patent Number: 6,111,138
[45] Date of Patent: Aug. 29, 2000

[54] PROCESS FOR PREPARING UREA

[75] Inventors: Julius G. T. Van Wijck, Maastricht; Jozef H Meessen, Gulpen, both of Netherlands

[73] Assignee: DSM N.V., Heerlen, Netherlands

[21] Appl. No.: 09/361,710

[22] Filed: Jul. 28, 1999

Related U.S. Application Data

[63] Continuation of application No. PCT/NL98/00036, Jan. 20, 1998.

[30] Foreign Application Priority Data

Jan. 29, 1997 [NL] Netherlands ............................ 1005118

[51] Int. Cl.[7] .................................................. C07L 273/00
[52] U.S. Cl. .................................................. 564/65
[58] Field of Search ................................ 564/65

[56] References Cited

U.S. PATENT DOCUMENTS

| | | |
|---|---|---|
| 3,503,970 | 3/1970 | Kanai et al. . |
| 3,708,536 | 1/1973 | Hillenbrand . |
| 3,723,430 | 3/1973 | Kokubo et al. . |
| 4,433,146 | 2/1984 | Beckers et al. . |

FOREIGN PATENT DOCUMENTS

| | | |
|---|---|---|
| 2013682 | 7/1969 | France . |
| 8400839 | 10/1985 | Netherlands . |
| 1216100 | 12/1970 | United Kingdom . |
| 1 309 275 | 3/1973 | United Kingdom . |
| 1309275 | 3/1973 | United Kingdom . |

*Primary Examiner*—Paul J. Killos
*Attorney, Agent, or Firm*—Pillsbury Madison & Sutro LLP

[57] ABSTRACT

Process for the preparation of urea, in which the gas stream which is released during the synthesis of melamine and is composed essentially of ammonia and carbon dioxide is used to synthesize urea, in which process the gas stream which originates from a high-pressure melamine process and is composed essentially of ammonia and carbon dioxide is condensed at a pressure virtually equal to the pressure in the melamine reactor, in which process substantially anhydrous ammonium carbamate is formed, after which said ammonium carbamate is fed to a high-pressure section of a urea stripping plant.

17 Claims, No Drawings

PROCESS FOR PREPARING UREA

This application is a continuation of PCT/NL98/00036, filed Jan. 20, 1998.

The invention relates to a process for preparing urea, in which the gas stream which is released during the synthesis of melamine and is essentially composed of ammonia and carbon dioxide is used for the synthesis of urea.

Such a process is described, inter alia, in GB-A-1,309,275. In the latter, a preparation of urea is disclosed in which the offgas which is essentially composed of ammonia and carbon dioxide and is obtained in the preparation of melamine in a high-pressure melamine process is used for the synthesis of urea. In this process, the gas stream from the gas/liquid separator of the melamine plant, which is essentially composed of ammonia and carbon dioxide, is transferred to a low-pressure section of a conventional high-pressure urea plant. In said low-pressure section, the ammonia and carbon dioxide originating from the melamine plant are reacted in an additional reactor to form a urea solution. Said urea solution is then increased in pressure and transferred to the high-pressure section of the same urea plant.

Urea can be prepared by passing ammonia and carbon dioxide at a suitable pressure (for example, 12.5–35 MPa) and a suitable temperature (for example, 160–250° C.) into a synthesis zone in which ammonium carbamate is first formed according to the reaction

$$2NH_3 + CO_2 \rightarrow H_2N\text{---}CO\text{---}ONH_4$$

From the ammonium carbamate formed, urea is then formed by dehydration according to the equilibrium reaction:

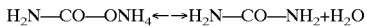

$$H_2N\text{---}CO\text{---}ONH_4 \leftrightarrow H_2N\text{---}CO\text{---}NH_2 + H_2O$$

The extent to which this conversion proceeds is dependent, inter alia, on the temperature and the excess of ammonia used. In this process, a solution which is composed essentially of urea, water, ammonium carbamate and unreacted ammonia is obtained as the reaction product. The ammonium carbamate and the unreacted ammonia have to be removed from the solution and are in most cases fed back to the synthesis zone. The synthesis zone may comprise separate zones for the formation of ammonium carbamate and urea. However, these zones may also be combined in one apparatus.

A conventional high-pressure urea plant is understood to be a urea plant in which the decomposition of the ammonium carbamate not converted into urea and the expulsion of the usual excess of ammonia takes place at a substantially lower pressure than the pressure in the synthesis reactor itself. In a conventional high-pressure urea plant, the synthesis reactor is usually operated at a temperature of 180–210° C. and a pressure of 18–30 MPa. In a conventional high-pressure urea plant, the unreacted reactants are fed back, after expansion, dissociation and condensation, at a pressure of between 1.5 and 10 MPa to the urea synthesis. Furthermore, in the case of a conventional high-pressure urea plant, ammonia and carbon dioxide are fed directly to the urea reactor. The molar $NH_3/CO_2$ ratio (=N/C ratio) in the urea synthesis is between 3 and 5 in a conventional high-pressure urea process.

The disadvantage of the process described in GB-A-1,309,275 is that an additional reactor is necessary because the gas stream which is fed from the melamine plant and which is composed essentially of ammonia and carbon dioxide is at too low a pressure, even in the case of a high-pressure melamine process, to be used directly in a conventional high-pressure urea plant. Furthermore, the process according to GB-A-1,309,275 requires an additional pump which transfers the urea produced at a low pressure to the high-pressure section.

The object of the invention is to find a process which does not have these disadvantages.

The applicant has found that said disadvantages can be eliminated by condensing the gas stream originating from the high-pressure melamine process, which is essentially composed of ammonia and carbon dioxide, at a pressure virtually equal to the pressure in the melamine reactor, in which process substantially anhydrous ammonium carbamate is formed, after which said ammonium carbamate is fed to a high-pressure section of a urea stripping plant.

A urea stripping plant is understood to be a urea plant in which the decomposition of the ammonium carbamate not converted into urea and the expulsion of the normal excess of ammonia take place mostly at a pressure which is essentially almost equal to the pressure in the synthesis reactor. This decomposition/expulsion takes place in a stripper, optionally with the addition of a stripping medium. In a stripping process, carbon dioxide and/or ammonia can be used as stripping medium before said components are metered to the reactor. Said stripping takes place in a stripper placed downstream of the reactor in which the solution which originates from the urea reactor and which contains, in addition to urea, ammonium carbamate, water, ammonia and carbon dioxide, is stripped with heat being fed. It is also possible to use thermal stripping here. Thermal stripping means that ammonium carbamate is decomposed and the ammonia and carbon dioxide present are removed from the urea solution exclusively by means of supplying heat. The streams which are released from the stripper and contain ammonia and carbon dioxide are fed back via a high-pressure carbamate condenser to the reactor. The reactor, the stripper and the high-pressure carbamate condenser form the most important components of the high-pressure section of a urea stripping plant. In a urea stripping plant, the synthesis reactor is preferably operated at a temperature of 160–220° C. and a pressure of 12.5–17.5 MPa. In the case of a stripper plant, the N/C ratio in the synthesis is between 2.5 and 4.

The substantially anhydrous carbamate stream from the condenser from the high-pressure melamine process is fed to a high-pressure section of a urea stripper plant and can be fed, for example, to a urea reactor, to a stripper, to a high-pressure carbamate condenser or to lines present between these. Preferably, the substan-tially anhydrous carbamate from the condenser of the high-pressure melamine process is fed directly to the urea reactor.

The condensation can be carried out in a condenser which is operated at a pressure which is substantially equal to the pressure in the melamine reactor. Preferably, the condenser is designed as a heat exchanger. In this case, a coolant is fed to the jacket side and the gas stream composed of carbon dioxide and ammonia is fed through the tube bundle. It is also possible to feed the gas stream through the jacket and the coolant through the tube bundle. Since the condensation temperature in said condenser is between 100 and 230° C., vaporizing boiler feed water can be used as coolant, which has the additional advantage that the heat of condensation can profitably be used to produce low-pressure steam (0.3 to 1.0 MPa). If no profitable use is present in the plant surroundings for said low-pressure steam, cooling water can also, of course, be used as coolant.

The advantage of the use of a carbamate stream from the high-pressure melamine plant is that a substantially anhydrous carbamate stream is obtained for the urea stripper plant which, as a result of its substantially anhydrous nature, ensures an improved efficiency in the urea plant compared with a urea plant which obtains a water-containing carbamate stream from the melamine plant. An additional advantage can be obtained by feeding the substantially anhydrous carbamate stream directly to the urea reactor.

The pressure of the carbamate flow originating from the condenser of the high-pressure melamine plant is between 5 and 80 MPa, preferably between 8 and 40 MPa. In particular, the pressure of the carbamate stream originating from the high-pressure melamine plant is 0–10 MPa and, more particularly, 0–2 MPa higher than the pressure in the urea reactor. The temperature of said carbamate stream is between 100 and 230° C., preferably between 140 and 200° C.

Urea synthesis

A frequently used embodiment for the preparation of urea by means of a stripping process is described in European Chemical News, Urea Supplement of Jan. 17, 1969, pages 17–20. In this process, the urea synthesis solution formed in the synthesis zone at a high pressure and temperature is subjected at synthesis pressure to a stripping treatment by being brought into contact with gaseous carbon dioxide in countercurrent, with heat being fed. In this process, most of the ammonium carbamate present in the solution decomposes into ammonia and carbon dioxide. These decomposition products are expelled in gaseous form from the solution and removed together with a small amount of water vapour and the carbon dioxide used for the stripping. In addition to carrying out such a stripping treatment with carbon dioxide as described in this publication, it is also possible to carry out the treatment thermally or with gaseous ammonia as stripping gas or with a mixture of the said gases. The gas mixture obtained in the stripping treatment is for the greater part condensed and adsorbed in a high-pressure carbamate condenser, after which the ammonium carbamate formed in this process is fed to the synthesis zone for the formation of urea. It is possible to carry out the synthesis in one reactor or two reactors. The stripping of the urea synthesis solution with a stripping medium can also take place in more than one stripper.

The high-pressure carbamate condenser can, for example, be designed as a so-called flooded condenser as described in NL-A-8400839. In this case, the gas mixture to be condensed is fed into the jacket space of a tube exchanger, into which jacket space a dilute carbamate solution is also fed, and the heat of solution and condensation released is removed with the aid of a medium flowing through tubes, for example water, which is converted in this process into low-pressure steam. The flooded condenser may be arranged horizontally or vertically. However, particular advantages are offered by carrying out the condensation in a horizontally arranged flooded condenser (a so-called pool condenser; see, for example, Nitrogen No. 222, July–August 1996, pages 29–31) since, compared with a vertically arranged flooded condenser, the liquid generally has a longer residence time in the condenser. As a result urea formation occurs, which has the effect of increasing the boiling point so that the temperature difference between the urea-containing carbamate solution and the coolant becomes greater, as a result of which a better heat transfer is effected. It is also possible to incorporate the condensation zone and the synthesis zone in one apparatus, as described in for example NL-A-1000416. In this case, the formation of ammonium carbamate and urea from carbon dioxide and ammonia is carried out at a pressure of 12.5–35 MPa in a urea reactor. The said urea reactor comprises a horizontally arranged condensation zone and a heat exchanger (a so-called pool reactor; see, for example, Nitrogen No. 222, July–August 1996, pages 29–31) in which ammonia and carbon dioxide are fed to the reactor and largely adsorbed in the urea synthesis solution. A substantial part of the heat produced by the condensation is removed with the aid of the heat exchanger. The residence time of the urea synthesis solution in the reactor is chosen so that at least 85% of the theoretically obtainable quantity of urea is prepared, after which the urea synthesis solution is processed to form a urea solution or solid urea.

After the stripping process, the stripped urea synthesis solution is let down to a low pressure and evaporated, and the urea melt obtained in this process is completely or partly transferred to the melamine plant.

Melamine synthesis

The preparation of melamine preferably starts from urea as raw material, preferably in the form of a melt. Ammonia and carbon dioxide are by-products during the melamine preparation, which proceeds according to the following reaction equation:

$$6CO(NH_2)_2 \rightarrow C_3N_6H_6 + 6NH_3 + 3CO_2$$

The preparation can be carried out at a pressure of between 5 and 80 MPa without the presence of a catalyst. The temperature of the reaction is between 300 and 500° C. and is preferably between 350 and 425° C.

A device for the preparation of melamine which is suitable for the present invention may comprise, for example, a melamine scrubber, a reactor, optionally combined with a gas-liquid separator or having a separate gas-liquid separator, optionally an afterreactor or ageing vessel placed downstream of the reactor, and a product cooler/product working-up section. Placed downstream of the melamine scrubber is a condenser for converting the gas stream originating from the melamine scrubber into substantially anhydrous ammonium carbamate.

In one embodiment of the process, melamine is produced from urea in a device comprising, for example, a condenser, a melamine scrubber, a reactor for the production of melamine, optionally an afterreactor or ageing vessel and a product cooler. In this case, urea melt is fed from the urea plant to a melamine scrubber at a pressure of 5–80 MPa, preferably 8–40 MPa, and at a temperature above the melting point of urea. Said melamine scrubber can be provided with a jacket in order to provide additional cooling in the scrubber. The melamine scrubber may also be provided with internal cooling bodies. In the melamine scrubber, the liquid urea comes into contact with reaction gases from the melamine reactor or from a separate separator placed downstream of the reactor. The reaction gases are composed essentially of carbon dioxide and ammonia and also contain a quantity of melamine vapour. The molten urea scrubs the melamine vapour out of the offgas and carries said melamine back to the reactor.

The offgases composed essentially of ammonia and carbon dioxide are removed from the top of the melamine scrubber, converted into ammonium carbamate in a condenser and returned to the high-pressure section of a urea plant, in which urea is produced by means of the stripping process, in order to be used therein as a raw material for urea production.

The pressure of said carbamate stream is almost equal to the pressure in the melamine reactor and is between 5 and 80 MPa, preferably between 8 and 40 MPa. More particularly, the pressure is 0–10 Mpa higher than the pressure in the urea reactor and still more particularly 0–2 MPa higher than the pressure in the urea reactor.

The temperature of said carbamate stream is preferably between 140 and 200° C.

The preheated urea is removed from the melamine scrubber and fed, together with the scrubbed melamine, by means of, for example, a high-pressure pump to the reactor, which is at a pressure of 5 to 80 MPa and preferably of 8 to 40 MPa. In transferring the urea melt to the melamine reactor use can also be made of gravity by placing the melamine scrubber above the reactor.

In the reactor, the molten urea is heated to a temperature of 300 to 500° C., preferably of approximately 350 to 425° C., at a pressure of 5 to 80 MPa, preferably of 8 to 40 MPa, under which conditions the urea is converted into melamine, carbon dioxide and ammonia.

A quantity of ammonia can be metered to the reactor. The ammonia added may serve, for example, as a purging agent for preventing blockage of the reactor bottom or to avoid the formation of condensation products of melamine, such as melam, melem and melon or to promote the mixing in the reactor. The quantity of ammonia fed to the reactor is 0–10 mol per mole of urea, preferably 0–5 mol is used and in particular 0–2 mol of ammonia per mole of urea. The carbon dioxide and ammonia produced in the reaction, and also the ammonia additionally fed, collect in the separation section, for example in the top of the reactor, but a separate separator placed downstream of the reactor is also possible, and are separated in the gaseous state from the liquid melamine. The gas mixture produced is passed to the melamine scrubber to remove melamine vapour and to preheat the urea melt. The liquid melamine is removed from the reactor and, in this embodiment, is transferred, for example, to an afterreactor, but transfer directly to the product cooler is also possible.

If an afterreactor or ageing vessel is used, the liquid melamine is brought into contact with 0.01–10 mol of ammonia per mole of melamine and, preferably, 0.1–2 mol of ammonia per mole of melamine. The contact time in the afterreactor or in the ageing vessel is between 1 minute and 10 hours. The temperature and the pressure in the afterreactor or ageing vessel are almost the same as in the reactor in which urea is converted into melamine. The liquid melamine present in the afterreactor or ageing vessel is removed from the afterreactor or ageing vessel and transferred to a product cooler. In the product cooler, the liquid melamine is cooled by bringing it into contact with a coolant. Preferably ammonia, and in particular liquid ammonia, is chosen as the coolant. In this process, the melamine is converted into powdered form and is removed from the cooling unit via the bottom of the product cooler.

In yet another embodiment of the process according to the invention, an evaporation step is included between the reactor or, possibly, the afterreactor and the product cooler. In said evaporation step, liquid melamine is converted into gaseous melamine, in which process the by-products, such as, for example, melam, remain behind in the evaporator. The advantage of this is that the amount of by-products in the melamine is reduced. In this way, melamine having a very high degree of purity is obtained. It is also possible to meter in additional ammonia during the evaporation. According to this process, gaseous melamine is then cooled with ammonia in the product cooler.

The invention is explained in greater detail by reference to the following examples.

EXAMPLE 1

A gas stream of 53.6 kg/hour is transferred from the melamine scrubber to a condenser. The pressure of said gas stream is 8 MPa and the temperature is 186° C. The composition is as follows:

50.3 wt. % ammonia,
49.3 wt. % carbon dioxide,
0.2 wt. % water,
0.2 wt. % urea.

The pressure in the condenser is maintained at almost 8 MPa and the temperature is lowered. At a temperature of 144° C., almost complete condensation of the gas stream occurs. The liquid mixture produced is transferred by a pump to the high-pressure section of a urea synthesis.

EXAMPLE 2

A gas stream of 60 kg/hour is transferred from the melamine scrubber to a condenser. The pressure of said gas stream is 15 MPa and the temperature is 202° C. The composition is as follows:

50.3 wt. % ammonia,
49.2 wt. % carbon dioxide,
0.3 wt. % water,
0.2 wt. % urea.

The pressure in the condenser is maintained at virtually 15 MPa and the temperature is lowered. At a temperature of 166° C., almost complete condensation of the gas stream occurs. The liquid mixture produced is transferred directly to the high-pressure section of a urea synthesis and is fed there to the inlet of the high-pressure carbamate condenser.

EXAMPLE 3

A gas stream of 51.2 kg/hour is transferred from the melamine scrubber to a condenser. The pressure of said gas stream is 20 MPa and the temperature 207° C.

The composition is as follows:

50.4 wt. % ammonia,
49.2 wt. % carbon dioxide,
0.2 wt. % water,
0.2 wt. % urea.

The pressure in the condenser is maintained at almost 20 MPa and the temperature is lowered. At a temperature of 175° C., almost complete condensation of the gas stream occurs while at the same time steam of 0.3 MPa is generated. The liquid mixture produced is transferred directly to the high-pressure section of a urea synthesis and is fed there to the feed line of the urea reactor.

What is claimed is:

1. Process for the preparation of urea, in which the gas stream which is released during the synthesis of melamine and is essentially composed of ammonia and carbon dioxide is used to synthesize urea, characterized in that the gas stream which originates from a high-pressure melamine process and is essentially composed of ammonia and carbon dioxide is condensed at a pressure virtually equal to the pressure in the melamine reactor, in which process substantially anhydrous ammonium carbamate is formed, after which said ammonium carbamate is fed to a high-pressure section of a urea stripping plant.

2. Process according to claim 1, characterized in that the carbamate stream originating from a high-pressure melamine process is fed to a urea reactor, to a stripper, to a high-pressure carbamate condenser or to lines present between these.

3. Process according to claim 1, characterized in that the synthesis reactor in the urea plant is operated at a temperature of 160–220° C.

4. Process according to claim 1, characterized in that the synthesis reactor in the urea plant is operated at a pressure of 12.5–17.5 MPa.

5. Process according to claim 1, characterized in that the carbamate stream released from the melamine process is at a temperature of between 140 and 200° C.

6. Process according to claim 1, characterized in that the carbamate stream released from the melamine process is at a pressure of between 8 and 40 MPa.

7. Process according to claim 6, characterized in that the carbamate stream released from the melamine process has a pressure which is 0–10 MPa higher than the pressure in the urea reactor.

8. Process according to claim 7, characterized in that the carbamate stream released from the melamine process has a pressure which is 0–2 MPa higher than the pressure in the urea reactor.

9. A process for preparing urea in an integrated melamine synthesis-urea synthesis installation, the melamine synthesis being achieved in a high pressure melamine synthesis process and the urea synthesis being achieved in a urea stripping plant, with the urea stripping plant including a high pressure section, said high pressure section including a urea reactor, a carbamate condenser, a urea stripper, and interconnecting lines, comprising, in numerical order, the steps of:

(1) obtaining a gas stream from a high pressure melamine synthesis process, the high pressure melamine synthesis process comprising reacting an urea melt in a melamine reactor to produce melamine, carbon dioxide, and ammonia, with the melamine reactor having a first operating pressure of at least 5 MPa and a first operating temperature of at least 300° C., the gas stream consisting essentially of ammonia and carbon dioxide and having a pressure substantially equal to the pressure in the melamine reactor;

(2) condensing the gas stream to form a liquid substantially anhydrous ammonium carbamate stream;

(3) feeding the liquid substantially anhydrous ammonium carbamate stream directly to the high pressure section of the urea stripping plant; and (4) reacting at least the liquid substantially anhydrous ammonium carbamate stream in the urea stripping plant to produce urea.

10. A process for preparing urea according to claim 9, wherein step (3) further comprises feeding the liquid substantially anhydrous ammonium carbamate stream directly into the urea reactor, the urea reactor having a second operating pressure and a second operating temperature.

11. A process for preparing urea according to claim 10, wherein step (3) further comprises the urea reactor having a second operating pressure of at least 12.5 MPa and a second operating temperature of at least 140° C.

12. A process for preparing urea according to claim 9, wherein step (3) further comprises feeding the liquid substantially anhydrous ammonium carbamate stream directly into the carbamate condenser, the carbamate condenser reactor having a third operating pressure and a third operating temperature.

13. A process for preparing urea according to claim 12, further comprising the step of:

(3.1) feeding quantities of carbon dioxide and ammonia into the urea reactor, the quantities of carbon dioxide and ammonia being selected to achieve, in combination with the liquid substantially anhydrous ammonium carbamate stream, an N/C ratio within the urea reactor of at least 2.5.

14. A process for preparing urea according to claim 13, wherein the quantities of carbon dioxide and ammonia are selected to achieve, in combination with the liquid substantially anhydrous ammonium carbamate stream, an N/C ratio within the urea reactor of between 2.5 and 4.0.

15. A process for preparing urea according to claim 10, wherein step (3) further comprises feeding the liquid substantially anhydrous ammonium carbamate stream directly into the urea stripper, the urea stripper having a fourth operating pressure and a fourth operating temperature.

16. A process for preparing urea according to claim 9, wherein step (3) further comprises feeding the liquid substantially anhydrous ammonium carbamate stream directly into one or more of the lines interconnecting the urea reactor, carbamate condenser, or urea stripper.

17. A process for preparing urea according to claim 9, wherein said liquid substantially anhydrous ammonium carbamate stream has a water content of less than 0.5 wt. %, and an N/C ratio of between 2.5 and 3.

* * * * *